US012693195B2

(12) United States Patent
Veldt

(10) Patent No.: US 12,693,195 B2
(45) Date of Patent: Jul. 28, 2026

(54) AIR SAMPLE CHAMBER FOR AN ELECTROSTATIC PRECIPITATION DETECTOR SYSTEM

(71) Applicant: Durridge Company, Inc., Billerica, MA (US)

(72) Inventor: Mordecai Veldt, Nashua, NH (US)

(73) Assignee: Durridge Company, Inc., Billerica, MA (US)

( * ) Notice: Subject to any disclaimer, the term of this patent is extended or adjusted under 35 U.S.C. 154(b) by 522 days.

(21) Appl. No.: 18/241,202

(22) Filed: Aug. 31, 2023

(65) Prior Publication Data

US 2024/0077389 A1      Mar. 7, 2024

Related U.S. Application Data

(60) Provisional application No. 63/403,165, filed on Sep. 1, 2022.

(51) Int. Cl.
G01N 1/22 (2006.01)
G01N 33/00 (2006.01)
(52) U.S. Cl.
CPC ..... G01N 1/2202 (2013.01); G01N 2001/222 (2013.01); G01N 33/0036 (2013.01)
(58) Field of Classification Search
CPC ............. G01N 1/2202; G01N 33/0036; G01N 2001/222
See application file for complete search history.

(56) References Cited

U.S. PATENT DOCUMENTS

| | | | | |
|---|---|---|---|---|
| 3,679,311 | A * | 7/1972 | Van Dusen, Jr. .... | G01N 1/2202 96/417 |
| 4,649,760 | A * | 3/1987 | Wedding ................. | G05D 7/01 73/861.64 |
| 5,029,248 | A * | 7/1991 | Miyake ..................... | G01T 5/10 250/DIG. 2 |
| 5,489,780 | A * | 2/1996 | Diamondis ........... | G01N 23/00 250/DIG. 2 |
| 6,288,400 | B1 * | 9/2001 | Negro ..................... | G01T 1/178 250/382 |
| 2004/0232345 | A1 * | 11/2004 | Jagam ..................... | G01T 1/178 250/370.02 |
| 2009/0288475 | A1 * | 11/2009 | Ariessohn ............. | B01D 45/06 73/28.06 |
| 2017/0268994 | A1 * | 9/2017 | Kawai ..................... | G01N 21/05 |
| 2021/0364659 | A1 * | 11/2021 | Gordon ................. | G01T 1/1603 |
| 2023/0384463 | A1 * | 11/2023 | Sundal ..................... | G01T 1/248 |

* cited by examiner

*Primary Examiner* — Blake C Riddick
(74) *Attorney, Agent, or Firm* — Barnes & Thornburg LLP

(57) ABSTRACT

Air sample chamber designs for improving electrostatic detection of particles by increasing the sensitivity of detecting radon gas in an air sample chamber. Examples includes convex shaped conductive elements disposed around a detector surface within an electrostatic participation detector chamber that form an effective electrostatic lens arrangement that increases an angle from which particles in the chamber are directed to the detector surface, which thereby increases the volume of the chamber above the detector surface from which charged particles can be captured.

20 Claims, 11 Drawing Sheets

AIR SAMPLE CHAMBER FOR AN ELECTROSTATIC PRECIPITATION DETECTOR SYSTEM

CROSS-REFERENCE TO RELATED APPLICATIONS

This application claims priority to and the benefit of U.S. Provisional Application Ser. No. 63/403,165, entitled "AIR SAMPLE CHAMBER FOR A DETECTOR SYSTEM," and filed Sep. 1, 2022, the contents of which is incorporated by reference herein in its entirety.

FIELD

The present disclosure relates to air sample chamber designs for improving electrostatic detection of particles, and more particularly to devices, systems, and methods for increasing the sensitivity of detecting radon gas in an air sample chamber by increasing an angle from which particles in the chamber can be captured by the sensor.

BACKGROUND

The detection of radon gas using electrostatic forces represents a sophisticated and innovative approach to addressing a crucial public health concern. Radon is a colorless, odorless, and tasteless radioactive gas that naturally emanates from the decay of uranium in soil and rocks. Prolonged exposure to elevated radon levels has been linked to an increased risk of lung cancer, making its detection of paramount importance.

Traditional methods for radon detection involve using alpha particle detectors or charcoal canisters to measure the radioactive decay products of radon. While effective, these methods often require complex equipment at remote laboratories and time-consuming procedures, often only providing an average reading after the samples have been evaluated. This has driven the need for more efficient and sensitive detection techniques, leading to the exploration of electrostatic-based approaches.

The concept of using electrostatic forces for radon detection builds upon the fundamental principle that charged particles can be manipulated and measured through electrical fields. In this context, radon gas and its decay products can be ionized to carry a net electric charge. Once ionized, particles can be influenced by electric fields.

One of the pioneering methods in electrostatic radon detection involves employing an ionization chamber. An ionization chamber consists of two electrodes separated by a small gap filled with a specific gas mixture. When radon and its progeny enter the chamber, the emitted alpha particles ionize the gas molecules, generating positively charged ions. An applied electric field then causes these ions to drift towards the negatively charged electrode, creating a measurable electric current. The concentration of radon can be inferred by quantifying the resulting current.

Another innovative approach exploits the use of electrostatic precipitation techniques that capitalizes on the principles of electrical attraction to identify and measure radon particles by capturing positively charged decay products, such as polonium 218, and measuring their subsequent emission of alpha particles due radioactive decay. Electrostatic precipitation techniques involve creating an electric field within a detection chamber that attracts and captures radon decay products onto a collection surface. When radon gas is present in the chamber, a portion decays into positively charged ions. These ionized particles, carrying a net electric charge, are then drawn towards a collection surface by the electric field. The process resembles the way dust particles in the air are attracted to surfaces during static electricity buildup. As radon decay particles move towards the collection surface, they adhere to it, effectively being "precipitated" out of the air. This accumulation of radon decay products on the collection surface provides a measurable indicator of radon presence and concentration. Subsequent analysis of the collected particles using alpha spectrometry on the collection surface can measure the concentration of radon gas in the chamber.

Electrostatic precipitation offers several advantages, including simplicity and sensitivity. The method does not require complex equipment or elaborate setups, making it suitable for various applications, from personal radon monitors to larger-scale detectors. Electrostatic precipitation methods can operate in real-time, providing rapid and accurate measurements of radon levels. Additionally, they can be integrated into compact and portable devices, enabling widespread monitoring in various settings, including homes, workplaces, and public spaces. Precipitating the decay products directly onto a detector surface also reduces significantly any energy loss or 'straggling' of the alpha particles being measured. This greatly improves the spectral resolution, allowing long-term decay products to be excluded practically from real-time results.

However, directing charged ions onto the detector surface is challenging, and this challenge limits the size and shape of detection chambers that can be used, as well as the detector geometry and location within the chamber. Existing techniques employ simple air sample chamber shapes, such as a cylinder with a hemisphere end. These conventional shapes result in inefficient collection of the particles such that many of the particles do not reach the target, resulting in reduced count rates and, therefore, reduced statistical certainty and negatively affecting the minimum detection limits. Accordingly, there exists a need to improve the ability to direct charged ions onto a collection surface with an electrostatic precipitation detection chamber.

SUMMARY

Electrostatic collection of particles (such as the decay products of radon and thoron) for immediate or future evaluation and detection is an established technique, but is often employed with simple air sample chamber shapes, such as a cylinder with a hemisphere end. These conventional shapes result in inefficient collection of the particles such that many of the particles do not reach the target, resulting in reduced count rates, therefore reduced statistical certainty, and thereby negatively affecting the minimum detection limits.

Examples of the present disclosure include an electrostatic precipitation instrument that includes a conductive vessel defining a volume configured to receive a gaseous fluid sample, the conductive vessel defining an interior region of the volume configured to have a particle detector disposed therein, a detector surface disposed within the interior region and configured to detect particles thereon, where the conductive vessel and the detector surface are configured to maintain a voltage difference therebetween, the voltage difference generating electric field lines along which charged particles within the volume will be directed towards the detector surface, a portion of the field lines extending from an interior surface of the conductive vessel to the detector surface, and a conductive convex surface of an inner wall of the conductive vessel configured to increase the curvature of field lines above the detector surface and thereby define a portion of the volume of the conductive vessel from which charged particles within a gaseous fluid sample can be captured by the detector surface.

The conductive convex surface can configured to increase the curvature of the field lines above the detector surface with respect to the influence of adjacent inner surface regions of the conductive vessel. In some examples, the detector surface is configured to detect particles using alpha spectrometry. The conductive surface can forms a portion of an interior surface of the conductive vessel. The conductive convex surface can be integrally formed with adjacent inner surface portions of the conductive vessel. In some examples, the conductive convex surface encircles the detector surface such that the conductive convex surface is configured increase the curvature of the field lines away from an axis normal to the detector surface. The conductive vessel can defines a nominal width above the detector surface, and the conductive convex surface defines a width less than the nominal width. In some examples, the convex surface extends above a height of the detector surface. In some examples, conductive vessel has a circular cross-section and the conductive surface defines a circular ring about the detector surface.

Another example of the present disclosure is an electrostatic precipitation instrument for detecting radon gas that includes a conductive vessel defining a volume configured to receive a gaseous fluid sample, the conductive vessel defining a convex surface encircling an interior region of the volume configured to have a particle detector disposed therein, and a detector surface disposed within the interior region and configured to detect polonium particles thereon using alpha spectrometry. The conductive vessel and the detector surface are configured to maintain a voltage difference therebetween, the voltage difference generating electric field lines along which charged particles within the volume will be directed towards the detector surface, a portion of the field lines extending from an interior surface of the conductive vessel to the detector surface. And, when the voltage difference between the conductive vessel and the detector surface is established, the convex surface forms an electrostatic lens above the detector surface, the electrostatic lens being configured to influence the curvature of field lines above the detector surface and thereby define a portion of the volume of the conductive vessel from which charged particles from a gaseous fluid sample within conductive vessel can be captured by the detector surface.

In some examples, the conductive convex surface is configured to increase the curvature of the field lines above the detector surface with respect to the influence of adjacent inner surface regions of the conductive vessel. The conductive vessel can define a nominal width above the detector surface, and the conductive convex surface defines a width less than the nominal width. In some examples, the convex surface extends equal to or above a height of the detector surface. In some examples, the conductive vessel has a circular cross-section and the conductive surface defines a ring about the detector surface. In some examples, the convex surface defines a transition between a nominal width region of the conductive vessel and a reduced width region, and the detector surface is disposed within the reduced width region. In some examples, the conductive vessel defines a closed end having a hemispherical shape. In some examples, the detector surface is disposed opposite to the closed end with the surface facing the close end. In some examples, the instrument further includes an air handling system coupled with the chamber and configured to control delivery of gas into and out of the conductive vessel. In some examples, the detector surface is configured for real-time detection of radon gas in the volume of the conductive vessel. In some examples, the detector surface comprises a silicon-wafer-based detector configured to sense the emission energies of alpha particles emitted from particles captured on the target surface.

BRIEF DESCRIPTION OF DRAWINGS

This disclosure will be more fully understood from the following detailed description taken in conjunction with the accompanying drawings, in which.

DETAILED DESCRIPTION

Figure 1:
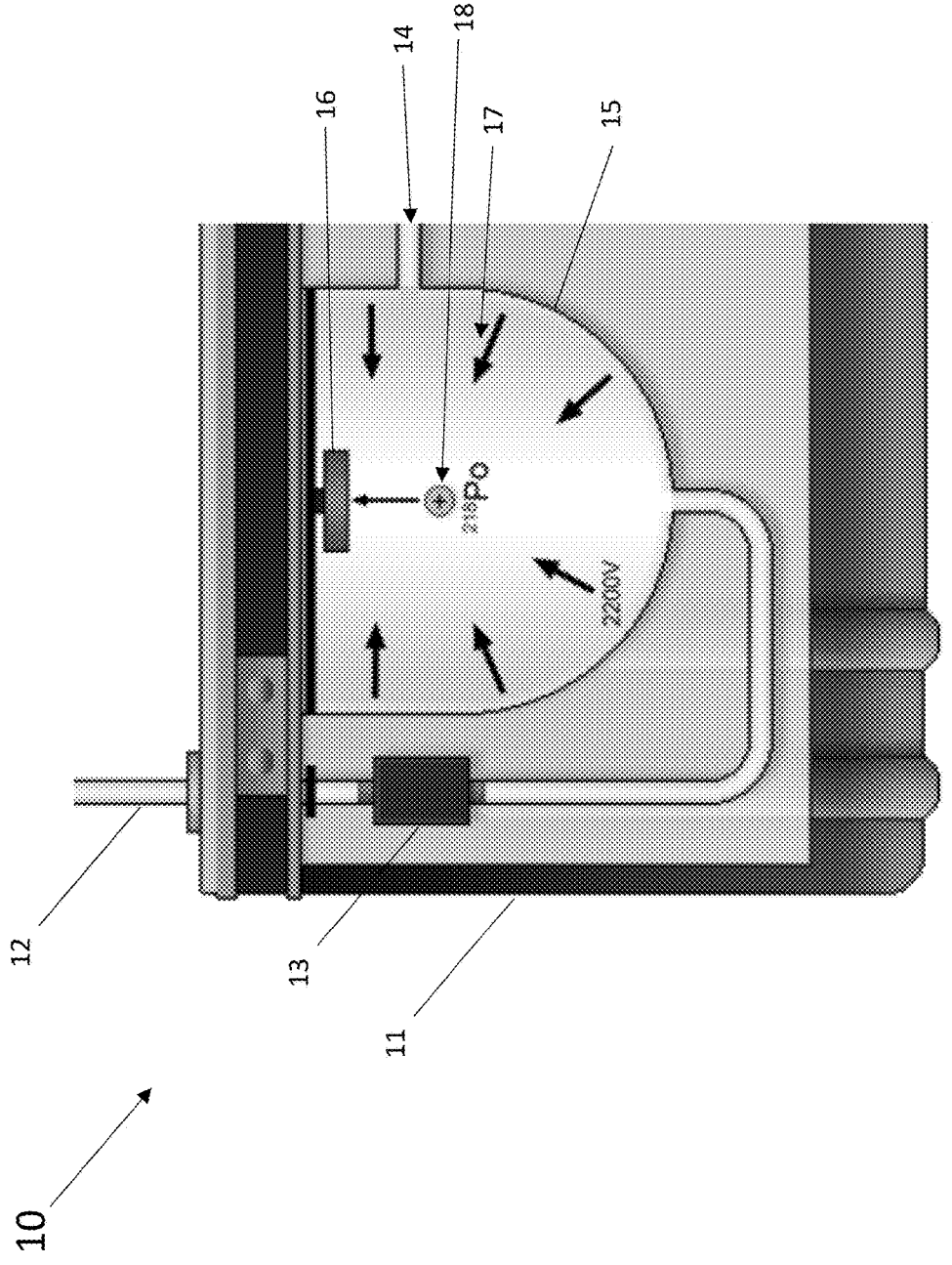
FIG. 1 is a cross-sectional schematic of a prior art radon detector system using electrostatic precipitation.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, components related to or otherwise part of such devices, systems, and methods specifically described herein and illustrated in the accompanying drawings are non-limiting embodiments and that the scope of the present disclosure is defined solely by the claims. The features illustrated or described in connection with one embodiment may be combined with the features of other embodiments. Such modifications and variations are intended to be included within the scope of the present disclosure. Some of the embodiments provided for herein may be schematic drawings, including possibly some that are not labeled as such but will be understood by a person skilled in the art to be schematic in nature. They may not be to scale or may be somewhat crude renderings of the disclosed components. A person skilled in the art will understand how to implement these teachings and incorporate them into systems, methods, and components related to each of the same.

To the extent the present disclosure includes various terms for components and/or processes of the disclosed devices, systems, methods, and the like, one skilled in the art, in view of the claims, present disclosure, and knowledge of the skilled person, will understand such terms are merely examples of such components and/or processes, and other components, designs, processes, and/or actions are possible. By way of non-limiting example, while the present application describes forming an electrostatic lens around a detector surface using curved portions of the detector chamber wall around the detector surface, alternatively, or additionally, the electrostatic lens can be formed using separate structures disposed within the detector chamber. In the present disclosure, like-numbered and like-lettered components of various embodiments generally have similar features when those components are of a similar nature and/or serve a similar purpose. To the extent terms such as front, back, top, bottom, forward, aft, proximal, distal, etc. are used to describe a location of various components of the various disclosures; such usage is by no means limiting, and is often used for convenience when describing various possible configurations.

The present disclosure is related to detector systems using electrostatic precipitation to capture and measure radioactive particles and their decay progeny (e.g., radon and polonium) to precisely estimate the radon content within the chamber and, by extension, within the environment from which the air was sampled. Examples of the present disclosure include detector systems with charged detector vessels that form electrostatic lenses about a detector region and thereby increase the volume of the chamber from which charged particles can be captured. For example, a hemispherical detector vessel with a detector surface facing the concave hemisphere surface and a convex region of the vessel surrounding the detector surface such that, above the detector surface, field lines—along which charged particles are directed to the detector—curve outward sharply to capture particles from a wide volume close to the surface. The present disclosure is not limited to these specific arrangements and shapes, but rather, these are examples. Examples of the present disclosure include electrostatic lenses arranged about a detector surface to increase the rate of volume growth above the detector from which charged particles are captured, thereby increasing an effective 'field of view' of the charged detector and vessel arrangement and increasing the volume efficiency for a given set of geometric constraints. The volume efficiency is specified as the ratio of the sample chamber where a charged particle is collected to the detector (versus the rest of the volume where charged particle is collected to a non-sensitive surface) to the total volume of the sample. The volume efficiency can also incorporate a weighting factor that models the reduced chance of a charged particle remaining charged the longer it spends travelling through the collection field. Random collisions can neutralize a particle so it is no longer collected by the electrostatic fields, so volume that is further from the collection surface is less able to increase the effective sensitivity.

Described herein are certain detector instruments and related technologies for measured the presence and concentration of radon gas using electrostatic precipitation to capture charged particles from a gas sample chamber and alpha spectrometry to measure the specific presence and concentration of different isotopes captured from the chamber. One example of an existing radon gas detector system using electrostatic precipitation and alpha spectrometry is the RAD7 Radon Detector available from Durridge Company, Inc. of Billerica, Massachusetts. FIG. 1 shows a cross-sectional schematic of the detector system 10 of the RAD7 device. The system 10 includes a housing 11 that contains a measurement chamber 15 with a detector structure 16 inside (e.g., a target surface and a holding surface to secure the target and maintain a voltage difference between the target surface and the chamber 15), and inlet 12 to the chamber 15, and outlet 14 from the chamber, and a pump/flow meter 13 that controls introduction of gas to the chamber 15. The measurement chamber 15 allows for the detection of certain particles by electrostatic precipitation of particles 18 onto the target surface of the detector structure 16. In operation, a strong voltage difference is created between the chamber 15 and the detector 16. As shown, this can be about 2200 volts and results in the formation of electric field lines 17 along with positively charged particles within the chamber will be drawn to the detector. While the RAD7 Radon Detector system 10 provides industry-leading performance, it is widely believed that the instrument cannot be made more sensitive without increasing the volume of the air sample or measurement chamber, which would result in a larger system that could be inconvenient and clumsy for portable use.

Aspects of the present disclosure include air sample chambers that use carefully designed geometry of the sample chamber around the detector surface and field-influencing elements to optimize the collecting electromagnetic field. Examples include forming convex surfaces in the chamber near the detector surface to create an effect similar to an electrostatic lens such that the peripheral field lines extends from the detector surface curve strongly away from the detector surface in the later direction, thereby increasing the volume of the detector chamber from which charged particles are captured. This can be considered an effective increase in the field of vision of the detector surface into the chamber. This careful control of the geometry can greatly improve the volumetric efficiency of a detector system, allowing increased system sensitivity with smaller sample volumes, and decreasing an average drift distance for a given sensitivity or number of collected particles. This can result in an instrument that is smaller and/or more sensitive than those presently in use.

While it is possible to design collection artifacts that are completely exposed (e.g., a wire in a cylinder), these typically require a separate step after collection to analyze the collected particles, and are thus not suitable for of real-time evaluation of electrostatically collected particles. Aspects of the present disclosure are for either active detectors, or passive targets that are analyzed later. Many real-time sensors exist for analyzing decay energies of collected radioactive particles, but most are constrained by manufacturing processes to be planar devices such as silicon-wafer-based detectors that, in accordance with processing industry norms, requires mounting, protection, and sometimes masking of edges of the detector. These necessary obstructions mean that simplistic chamber shape approaches end up with only a fraction of their sample volume effectively allowing its particles to reach the sensitive target. Aspects of the present disclosure include chamber geometries and/or field-effect elements that greatly increase the volume of the sample chamber from which charged particles can be electrostatically collected to a target area for sensing.

Aspects of the present disclosure include optimization for any geometry of the detector and any geometric constraints by using a novel approach of tracing electric field lines beginning from the sensitive area (e.g., a detector surface) backwards through a solved three-dimensional electric field that extends to the chamber wall. Examples include dividing the entire sample volume into cells or volume elements (e.g., voxels), each of which can be determined as being on a field line traced or not contributing to particles landing on the detector surface. This approach facilitates examining potential design geometries and evaluating them before physical prototyping. The exact impacts of geometry changes on electric field lines are nearly impossible to accurately intuit, so quantitatively analyzing the shape of the sample chamber and detector and any field shaping elements can improve the development of high performance sample chambers.

A further aspect of the present disclosure is the consideration of optimizing the transit time by, for example, evaluating particle travel distance along field lines and assigning a distance weighting function to 3D voxels. This allows for useful metrics of dome shape performance to be constructed, since in many cases a charged particle may be more likely to become electrically neutral the longer it has to travel to be collected, so volume elements further away should be weighted at a reduced rate compared to those near the detector. Design results that reflect optimizations of these considerations include the placement and/or formation of electrostatic lenses around the detector surface that shape the electric field lines, especially those from peripheral regions of the detector surface as those represent the maximum lateral extent of the sensor's collection from the chamber, Additionally, examples of the present disclosure include novel chamber shapes that improves manufacturability enables the use of low-capital cost hydroforming and metal spinning processes, which can result in a sample chamber structure that is rugged, chemically resistant, and capable of having inlet port fittings hermetically welded as an integral part of the sample chamber (e.g., due to the use of stainless steel as the chamber material). Welding of inlet port fittings in the chamber manufacturing process eliminates steps in the downstream production process of the final system that integrates the chamber, saving time and reducing human error and the potential for quality assurance problems.

Figure 2:
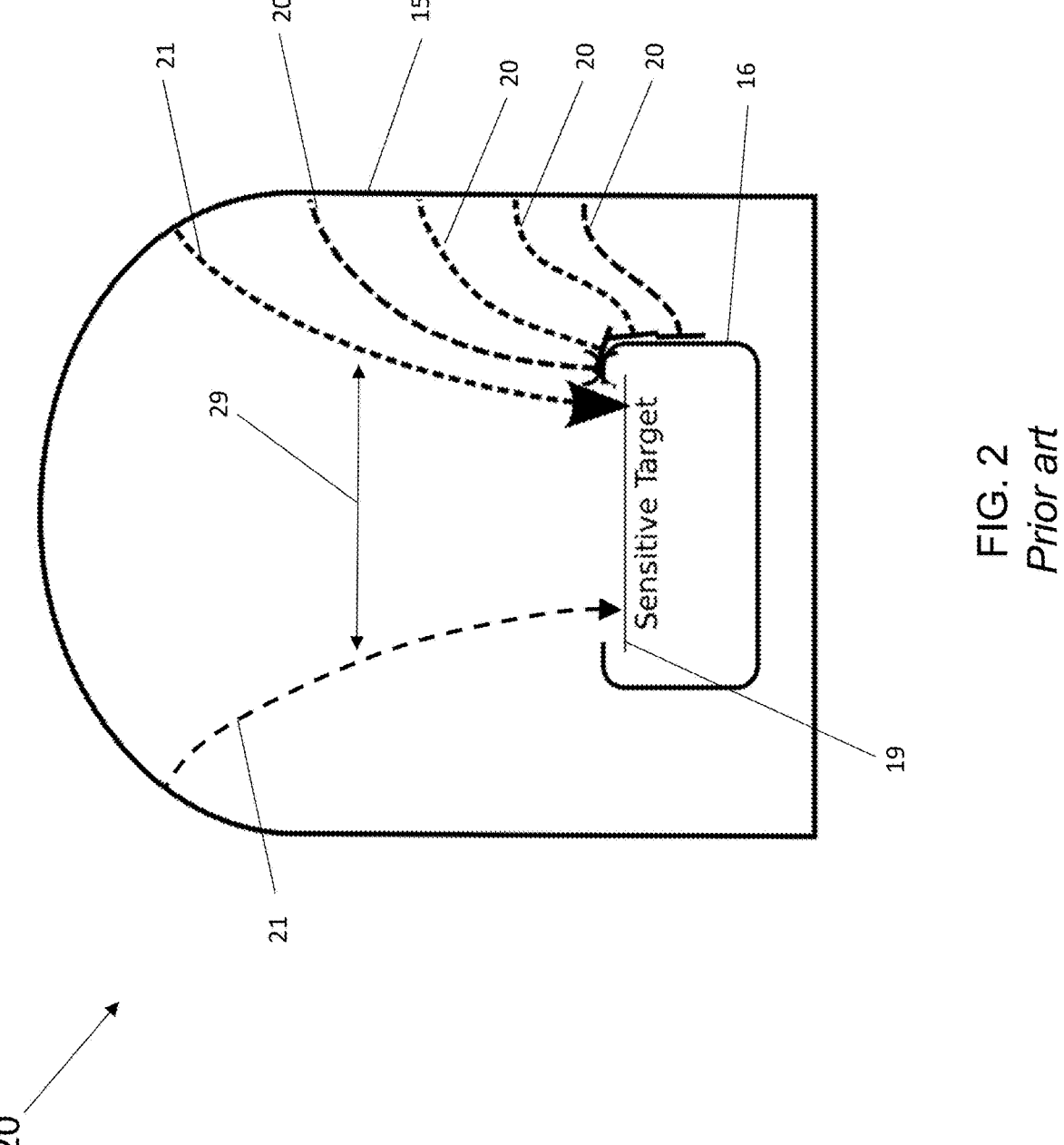
FIG. 2 is a cross-sectional schematic of a prior art electrostatic precipitation detector system, including a sensing surface disposed within an air sample chamber.

The following figures present a representative sampling of chamber designs that include convex regions formed around the detector surface to increase the volume of the chamber from which charged particles are captured, thereby increasing the sensitivity of the detector for a given chamber volume. FIG. 2 shows a prior art chamber design with electric field lines having a minimal lateral extension into the chamber above the detector surface in comparison to FIG. 3, which shows an example chamber of the present disclosure that includes convex electric-field-shaping regions formed in the chamber around the detector surface. FIG. 4 presents a comparison between the maximum lateral extending field lines of both the prior art design of FIG. 2 and the example chamber of FIG. 3. FIGS. 5A-5D illustrate a change in field line shape for a given chamber width by introducing field shaping elements according to the present disclosure, as well as, in FIGS. 5C and 5D, how the field shaping elements increase the sampling volume above the detector while decreasing the overall size of the detector chamber.

Precipitation Detector Chambers Forming Electrostatic Lenses

FIG. 2 shows the detector arrangement 20 of the prior art radon detector system 1 of FIG. 1. In FIG. 2, the chamber 15 (e.g., positively charged air sampling vessel), target holder 16 (e.g., negatively charged structure), and the detector target surface 19 (e.g., silicon structure configured for alpha spectrometry) are shown in cross-section. The chamber 15 has a cylindrical shape about the vertical axis (e.g., up and down with respect to the view) and the target holder 16 and target surface 19 can be similarly shaped or may be, for example, rectangular or another shape. FIG. 2 shows the electric field line 20, 21 that are created when a voltage difference is created between the chamber 15 and the target holder 16 and target 19. Charged particles present within the chamber 15 are directed to the target 19 so long as the field lines arrive on the target 19. As shown, a plurality of the generated field lines 20 do not arrive on the target 19 and instead impinge on the target holder 16. At the periphery of the target 19 field lines 21 of maximum lateral extend upward and outward from the target 19, herein also referred to as collection extent field lines. These field lines effectively define the maximum volume of the chamber 15 from which charged particles within the chamber 15 will be drawn to and arrive on the target surface 19. FIG. 2 shows a width 29 between the collection extent field lines 21 that represents this volume, herein after referred to as the capture volume. The rate of increase of this width 29 above the target surface 19 is a function of the shape of the electric field generated within the chamber 15.

Figure 3:
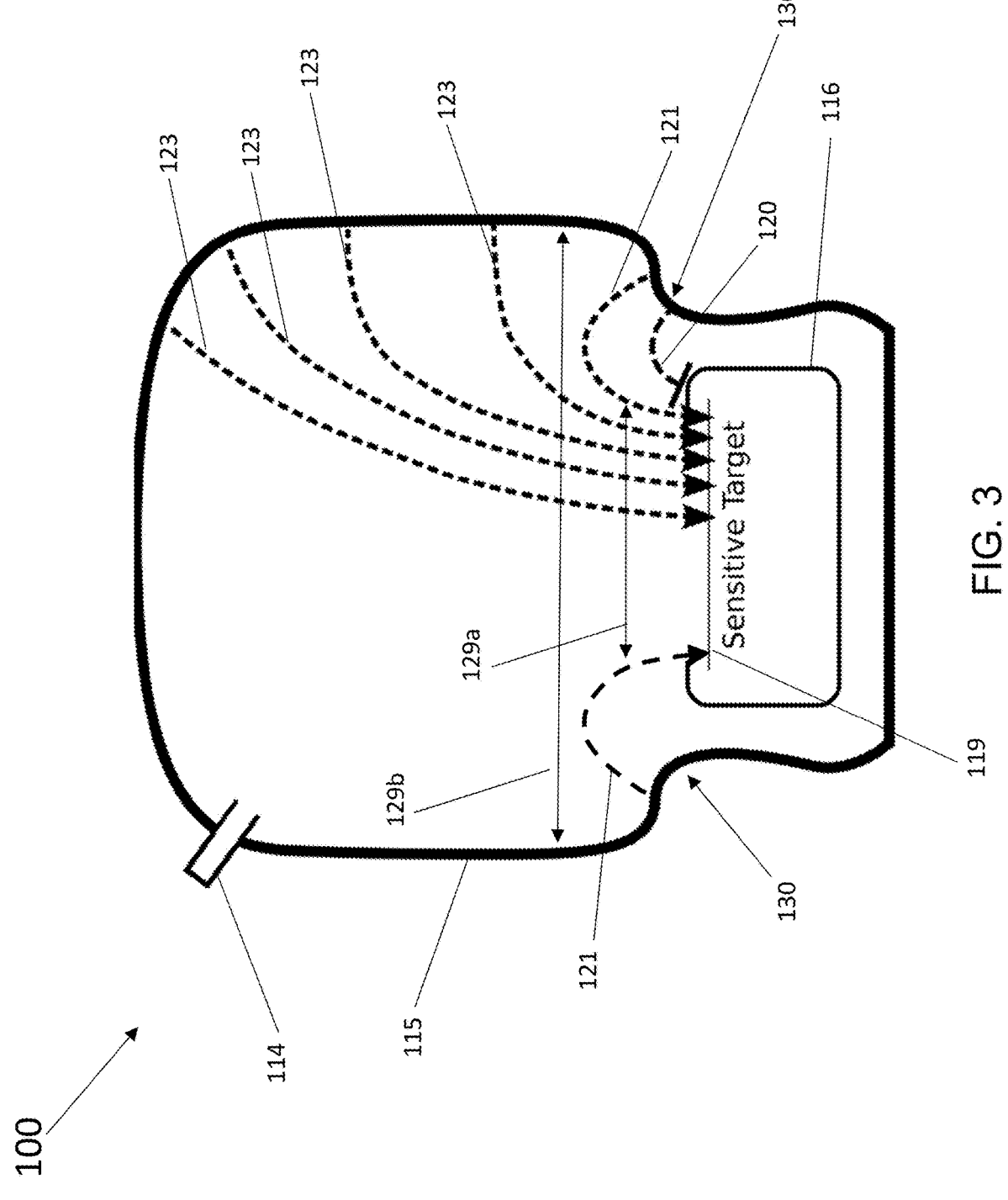
FIG. 3 is a cross-sectional schematic of an electrostatic precipitation detector system example of the present disclosure including an electrostatic lens formed in a chamber around a sensing surface.
Figure 4:
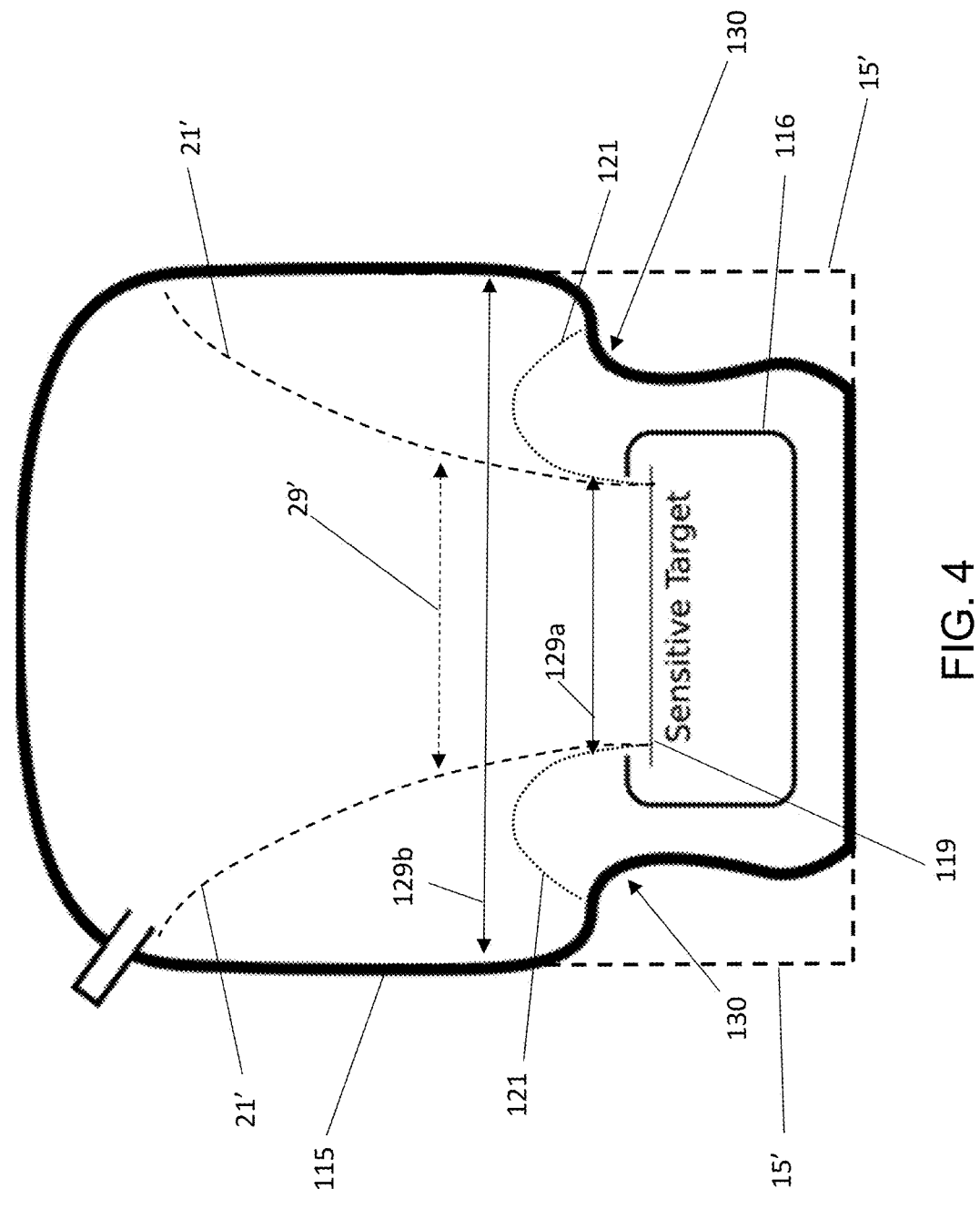
FIG. 4 is a cross-sectional schematic of the detector system of FIG. 3 compared with a detector system lacking an electrostatic lens formed in the chamber around the sensing surface.

FIG. 3 shows a detector system 100 example of the present disclosure. The system 100 includes a chamber 115 with a detector structure 116 disposed therein with a target surface 119 held by the detector structure. The detector structure 116 is disposed generally closer to one side of the chamber 15. This can be due to, for example, the target surface 119 having only a single-side for detecting particles, which is a typical condition of the sensors used for alpha spectrometry. FIG. 3 shows a plurality of representative field lines 120, 121, 123 that are created within the chamber 115 when a voltage difference is established between the chamber 15 and the detector structure 116 and target surface 119. Some of the field lines 120 impinge upon the detector structure 116, which indicates that charged particles captured and moved along those field lines 120 will not arrive upon the target surface 119. Other field lines 121, 123 do impinge upon the target surface 119, which indicates that charged particles captured and moved along those field lines 120 will arrive upon the target surface 119 and thereafter can be detected. The collection extent field lines 121 are shown and all field lines 123 within the collection extent field lines 121 are interior field lines 123 that show how all volume regions of the chamber 115 within the collection extent field lines 121 can transport charged articles to the target surface 119. The chamber 115 has formed therein a convex surface 130 that encircles the detector structure 116. The convex surface 130 extends inwardly towards the detector structure 116 with respect to the chamber structure 116. As shown, the convex surface 130 affects the field lines 120, 121, 123 and, specifically, substantially bends the collection extent field lines 121 laterally away from the target surface 119 above the detector structure 116. Accordingly, the capture volume 129a, 129b extends quickly above the target surface 119 from a minimum width 129a (e.g., approximately equal to the width of the target surface 119) to a maximum width 129b (e.g., approximately equal to the width of the chamber 115). The convex surfaces 130 significantly reduces the distance between the minimum width 129a and the maximum width 129b compared to prior art techniques.

FIG. 4 shows a comparison between the collection extent field lines 121 present with the system 100 of FIG. 3 to a chamber design without the convex surfaces 130. Differences between the naïve or conventional design and the design of the present disclosure are shown in FIG. 4. The conventional design, as illustrated in cross-section, consists of concave curves and straight lines. The exemplary embodiment of the present disclosure illustrated in FIG. 4, however, includes both concave and convex curved portions, along with straight or flat sections. These additional curves change the shape significantly, and present a region of the sample chamber wall that curves or includes a corner such that the surface has a normal vector, which points above horizontal, and a ledge, or shelf, approximately at the level of the detector.

In FIG. 4, the chamber 115 of FIG. 3 is shown with an overlay of a comparison chamber 15' that lacks the convex surfaces but otherwise has the same dimensions and detector structure 116 and target surface 119. The collection extent field lines 21' of the comparison chamber 15' are also overlaid with their capture volume 29'. As shown, both collection extent field lines 21', 121 extend upwards from the target surface 119, however the collection extent field lines 121 of the chamber 115 with convex surfaces 130 extend laterally outward at a significantly faster rate (per height above the target surface 119), thereby reaching their maximum width (e.g., the chamber width) at a distance that, in comparison to the capture volume 29' of the traditional design, results in a significantly larger (e.g., 70%) volume of the chamber 115 above the target surface 119 from which charged particles can by captured. In this comparison, the system 100 of the present disclosure increases the sensitivity of the chamber without increasing the overall size of the system (e.g., the convex hull). Further, the convex portions above the target surface 119 can be more than simple curves, and include, as shown, a radius that is very large at the top of the chamber 115, that becomes much smaller at the top left and right, becomes very large again along the sides of the chamber (indeed, the walls approach or reach straight). One advantage of the analytical approach to the design of this improved shape means that these curves can be as varied as the manufacturing process can permit, but the same essential features of a controlled field can be approximated with discrete radii for ease of describing the mechanical design. Again, in the illustrated conventional chamber 15', the conventional design lacks these radius transitions from high to low to high to low, and it lacks the feature of the shelf or ledge around the height of the detector as a focusing element.

These changes in shape increase the performance of the measurement chamber as well as the instrument that uses the measurement chamber. As used herein, "increase" means an improvement of at least about 10%, at least about 20%, at least about 30%, at least about 40%, at least about 60%, at least about 70%, at least about 80%, at least about 90%, at least about 100%, or at least about 50% with respect to sensitivity per unit volume of the chamber, meaning that overall sensitivity scales with the volume of the chamber.

Further, the chamber cost can be significantly reduced since the present disclosure enables a target sensitivity level to be achieved with a smaller chamber volume.

The present disclosure includes measurement chambers having the shaped described herein. It also includes detection instruments having the measurement chamber described herein. The measurement chamber can also be characterized as increasing the volumetric efficiency of the measurement chamber having a detector and being subject to an electric field. The measurement chamber having a detector and being subject to an electric field can also be characterized as improving (e.g., by reducing) the average drift distance for particles subject to collection. A detection instrument of the present disclosure having the improved measurement chamber can be characterized by improving measurement sensitivity for the same, or smaller, sample volume.

Aspects of the present disclosure include the shaping of electric field lines using conductive surfaces to increase the volume faction of an air-sampling chamber from which a target surface can receive charged particles. Shaping of electric field lines is a fundamental concept in electrostatics, an area of physics that deals with electric charges and their interactions. Conductive surfaces are materials that allow electric charges to move freely within them, such as metals. When a conductive surface is placed in an electric field, the free charges within the conductor redistribute themselves to achieve an equilibrium state. This redistribution leads to the formation of a new electric field within the conductor, which affects the original electric field lines.

The following describes the shaping of electric field lines with conductive surfaces of an air-sampling chamber. Given an external electric field, electric field lines extend outward from positive charges and terminate at negative charges. The shaping of electric field lines between conductive surfaces is a phenomenon that occurs when two or more conductive objects are brought close to each other and interact in the presence of electric charges. This interaction leads to changes in the distribution of electric field lines between the conductive surfaces, affecting the overall pattern of the electric field. If one of the conductive surfaces is charged, free charges within the conductors redistribute themselves to establish equilibrium. This redistribution results in the accumulation of charges on the surfaces facing each other. The presence of accumulated charges on the facing surfaces affects the distribution of electric field lines between the conductive surfaces. Electric field lines emanating from one surface curve and terminate on the other, creating a concentrated electric field between the surfaces. The density of these electric field lines is higher where the charges are more densely concentrated. This configuration stores electrical energy in the form of potential energy and this potential energy is used to move charged particles along the field lines. The shaping of electric field lines around convex surfaces involves the alteration of the path and distribution of electric field lines due to the curvature of the surface. Convex surfaces, which are outwardly curved, influence on how electric field lines interact and increases their concentration.

Aspects of the present disclosure utilize this increase in concentration to form an electrostatic lens around the target surface that increases the density of the field lines that extend from the target surface within the air-sampling chamber. Electrostatic lenses, generally, are structures that create controlled electric fields that can bend or focus the paths of charged particles, allowing them to converge towards a specific focal point. An electrostatic lens consists of one or more conductive electrodes with appropriate shapes and voltage potentials. In the present disclosure, the air-sampling chamber is a positively charged electrode and the target surface is negatively charged, thereby attracting positively charged ions within the air-sampling chamber. These electrodes create electric fields that exert forces on charged particles passing through them. By appropriately arranging the electrode geometry and voltages, the electric field can either deflect or focus the charged particles. For example, if a conductive surface is curved or shaped into a specific geometry near the target surface, the curves surface can influence the path of electric field lines near the target surface. This can be used to concentrate or guide electric fields in desired ways. To focus charged particles, examples of the present disclosure include air-sampling chambers that include an electrostatic lens designed to create an electric field that converges on a target surface within the air-sampling chamber. As charged particles enter and persist within the air-sampling chamber, the particles move with different initial trajectories. The charged particles are influenced by the presence of the electric field within the air-sampling chamber and are directed towards the negatively charged surfaces within the chamber, including the target surface. A portion of the air-sampling chamber has field lines that are concentrated by the electrostatic lens around the target surface and as charged particles within the chamber move within the region having field lines concentrated by lens, they experience forces that adjust their paths, causing them to converge toward the target surface. This convergence leads to the charged particles within the air-sampling chamber having their overall motion changed to arrive on the target surface.

Figure 5A:
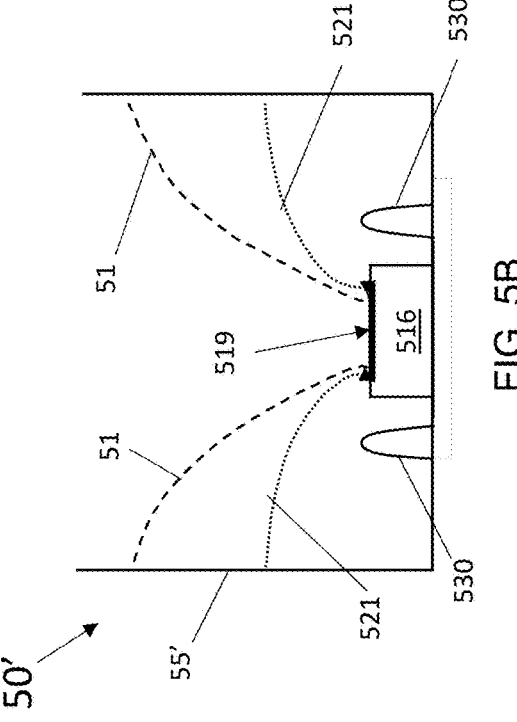
FIG. 5A is a cross-sectional schematic of a prior art electrostatic precipitation detector arrangement.
Figure 5B:
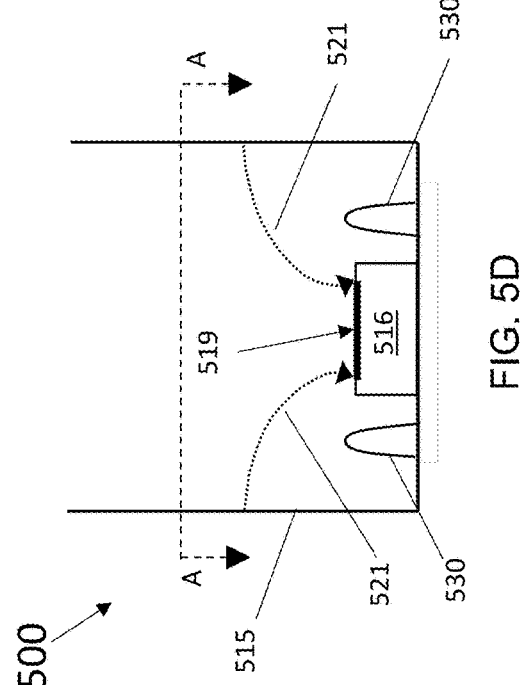
FIG. 5B is a cross-sectional schematic of an electrostatic precipitation detector arrangement of the present disclosure showing a comparison to the arrangement of FIG. 5A.

The use of electrostatic lenses enables a larger capture volume fraction for a given chamber size, where the capture volume fraction is defined as the volume within an air-sampling chamber from which charged particles are directed onto a target surface with respect to the total volume. Accordingly, this enables, for a given chamber size and with respect to prior art chamber designs without electrostatic lens elements, a greater sensitivity for a target surface to detect charged particles within the chamber (assuming equal distribution) and, alternatively, a given sensitivity to be maintained with a smaller chamber size. FIGS. 5A-5D illustrate this advantage. In FIG. 5A a prior art system 50 is illustrated with a detector structure 56 holding a target surface 59 within a chamber 55 configured for electrostatic precipitation detection of charged particles within the chamber 55. The collection extent field lines 51 impinging on the target surface 59 are shown. FIG. 5B shows an example system 50' modified using aspects of the present disclosure. The system 50' includes a chamber 55' that is the same size and shape as that chamber 50 of FIG. 5A, with a detector structure 516 and target surface 519 that are aligned with the system 50 of FIG. 5A as well. The difference in, in FIG. 5B, is the addition of a convex surface structure 530 disposed around the detector structure 516. The convex surface structure 530 can be, for example, a ring that encircles the detector structure 516 and/or the target surface 519 (as shown more clearly in FIG. 5E, with respect to the system of FIG. 5D), but could so be another shape and/or only partially or intermittently encircle the detector structure 516 and/or the target surface 519. In operation, with a voltage difference established between the chamber 55' and the target surface 519, the presence of the convex surface structure 530, which is also oppositely charged with respect to the target surface 519 (e.g., the convex surface structure 530 is conductive and integrally formed with the conductive chamber 55' or is otherwise oppositely charged from the target surface 519), bends the collection extent field lines 521 from the target surface 519 laterally away from the target surface more than the collection extent field lines 51 that are generated without the presence of the convex surface structure 530.

Figure 5C:
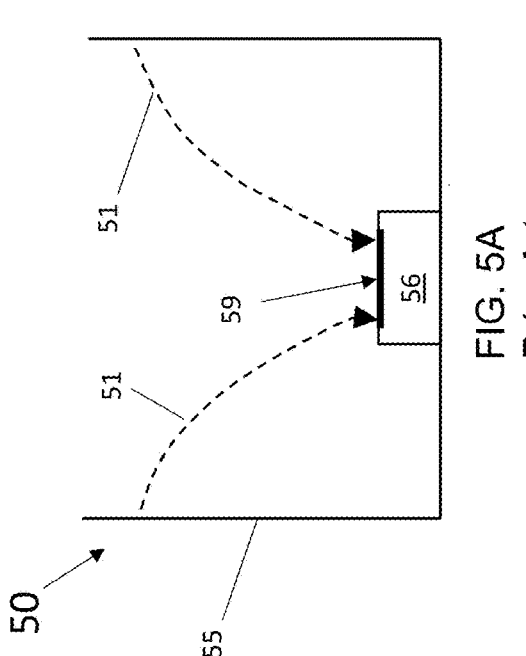
FIG. 5C is a cross-sectional schematic of another electrostatic precipitation detector arrangement of the present disclosure showing a comparison to the arrangement of FIG. 5A.
Figure 5D:
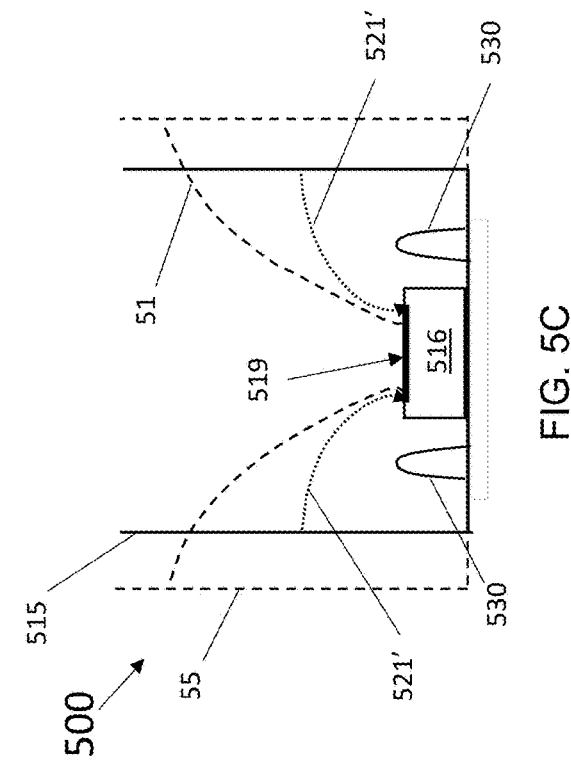
FIG. 5D is a cross-sectional schematic of the electrostatic precipitation detector arrangement FIG. 5C without the comparison chamber shown.
Figure 5E:
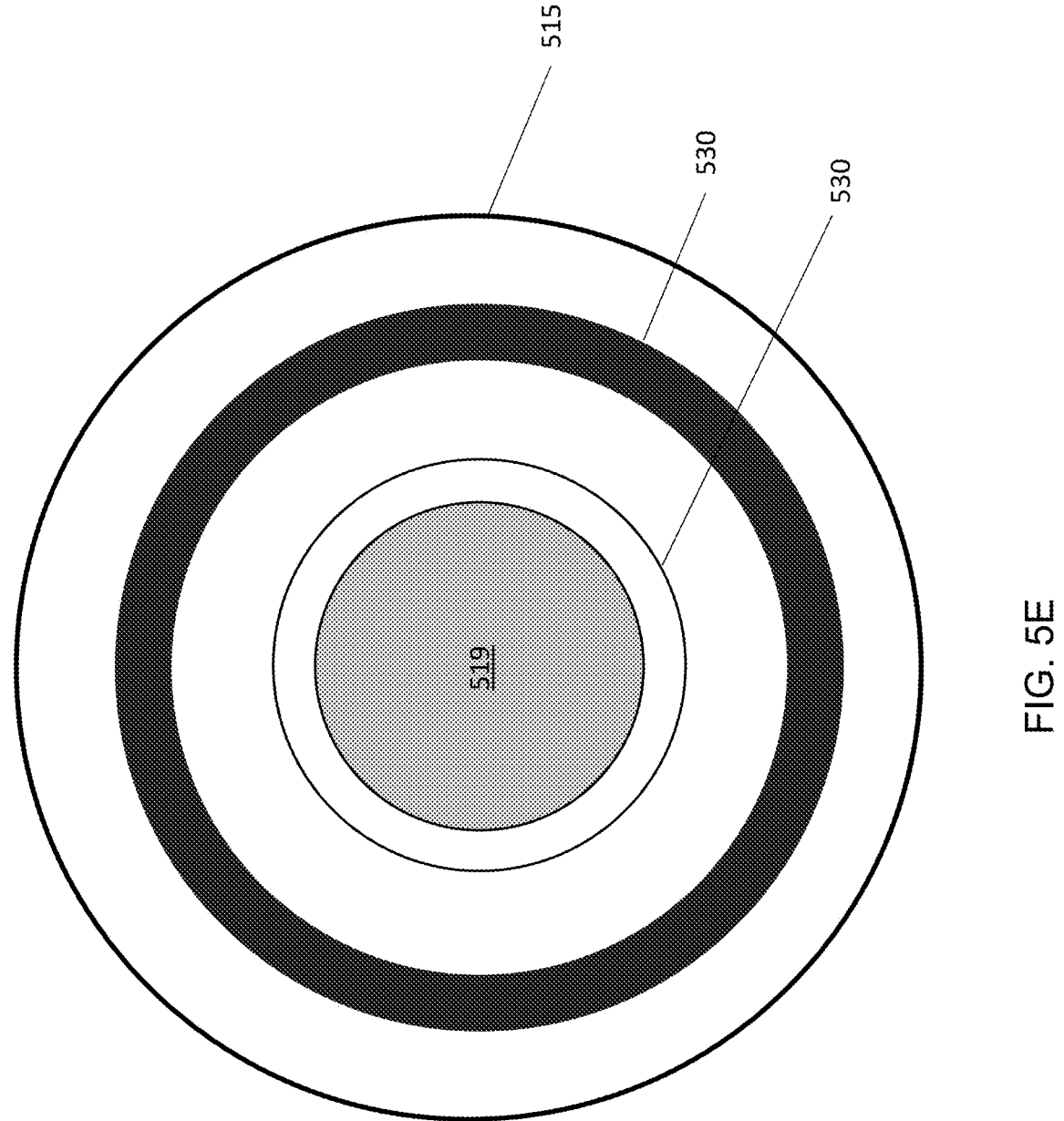
FIG. 5E is a top-down cross-sectional view of the electrostatic precipitation detector arrangement FIG. 5D.

Given that the volume of the chamber from which the target surface is able to received charged particles is an important parameter in the overall sensor design (e.g., a higher capture rate and thus a higher detection rate should result in increased detection sensitivity) the presence of the convex surface structure can improve performance of a detector system of a given size and/or be used to create a detector system or equal or greater performance but with less overall chamber size, as shown in FIG. 5C. In FIG. 5C a system 500 is shown with the same detector structure 516 and target surface 519 of the system 50' of FIG. 5B, but with a smaller overall chamber vessel 515. The chamber 55 and collection extent field lines 51 of the system 50 of FIG. 5A is shown with dotted lines to highlight the size difference and capture volume difference compared with the collection extent field lines 521' of the system 50'' of FIG. 5C. FIG. 5D shows the system 500 without comparisons and FIG. 5E shows a top-down cross-sectional view through the chamber along A-A, as indicated in FIG. 5D.

Figure 6A:
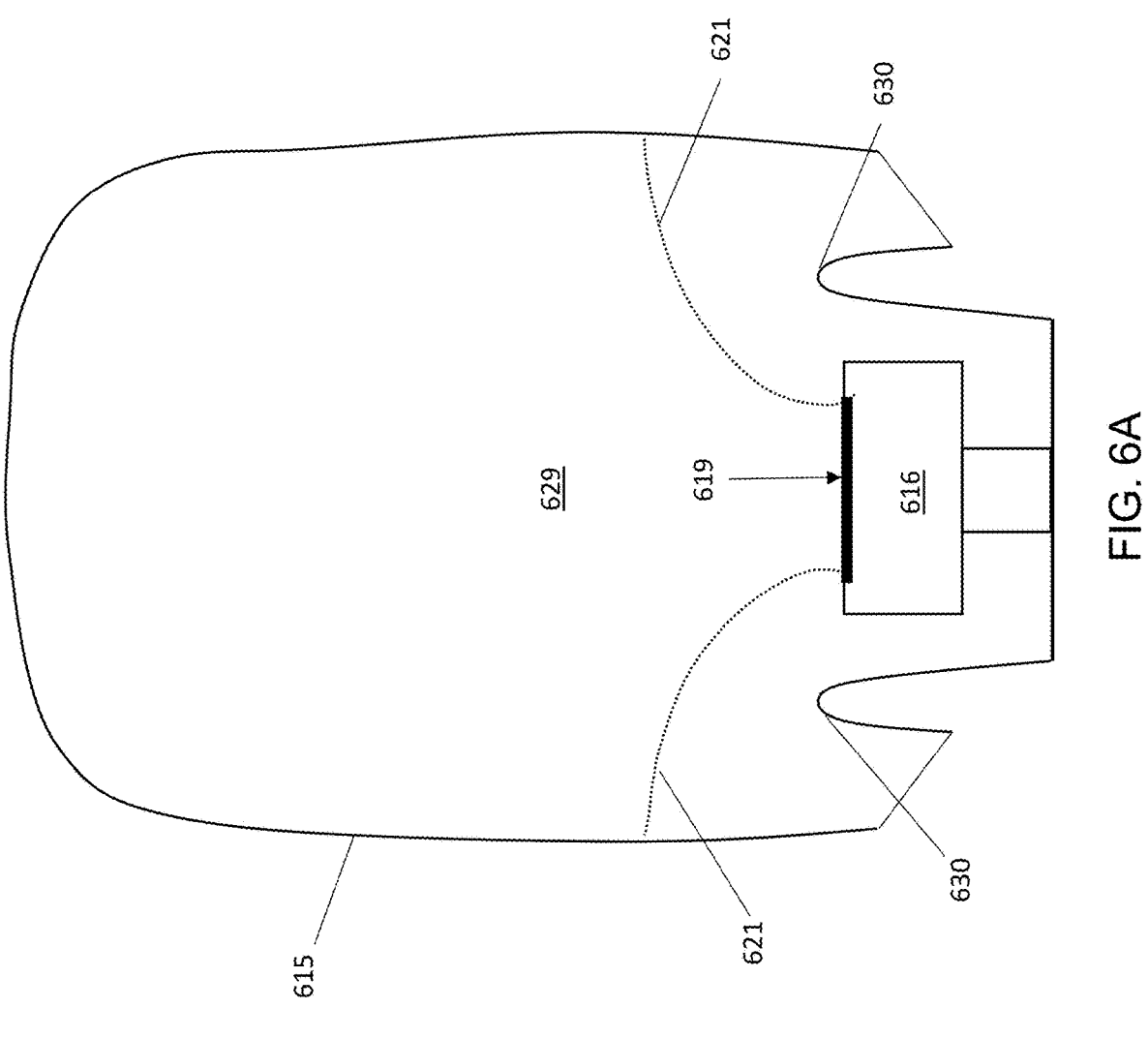
FIG. 6A is a cross-sectional schematic of another electrostatic precipitation detector example of the present disclosure.
Figure 6B:
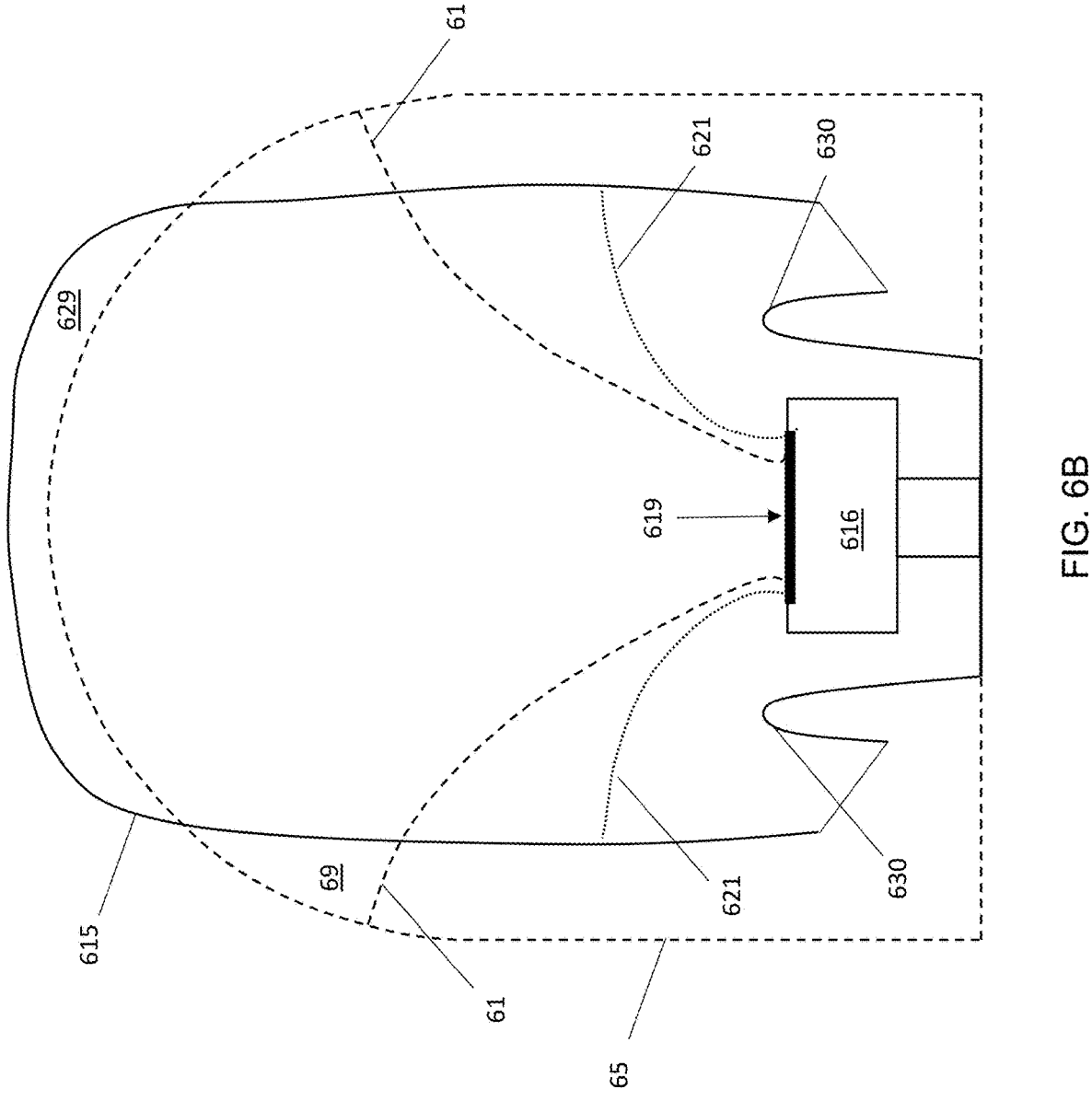
FIG. 6B is a cross-sectional schematic of the electrostatic precipitation detector system of FIG. 6A compared with a system lacking an electrostatic lens arrangement.

FIG. 6A shows another example system 600 of the present disclosure that includes a detection chamber 615 with a hemispherical shaped end and an opposing end with a detector structure 616 and target surface 619 arranged to face the hemispherical end of the chamber 615. The chamber 615 includes a convex ring structure integrally formed therein that encircles the target surface 619 and extends into the chamber to dispose an apex of the convex ring structure at a location sufficient to bend the collection extent field lines 621 from the target surface 619 laterally away to increase the capture volume 629 of the chamber 615 when a potential difference is established between the chamber 615 and the target surface 619. FIG. 6B shows a comparison between the system 600 of FIG. 6A and a traditional system design that includes a hemispherical chamber 65 of similar size with the same detector structure 616 and target surface 619 disposed therein. The collection extent field lines 61 between the hemispherical chamber 65 and target surface 619 are shown, as well as the resultant capture volume 69. Precise physics simulations of both chambers was conducted to calculate the field lines 61, 621 and a comparison result from these simulations is shown in FIG. 6C.

Figure 6C:
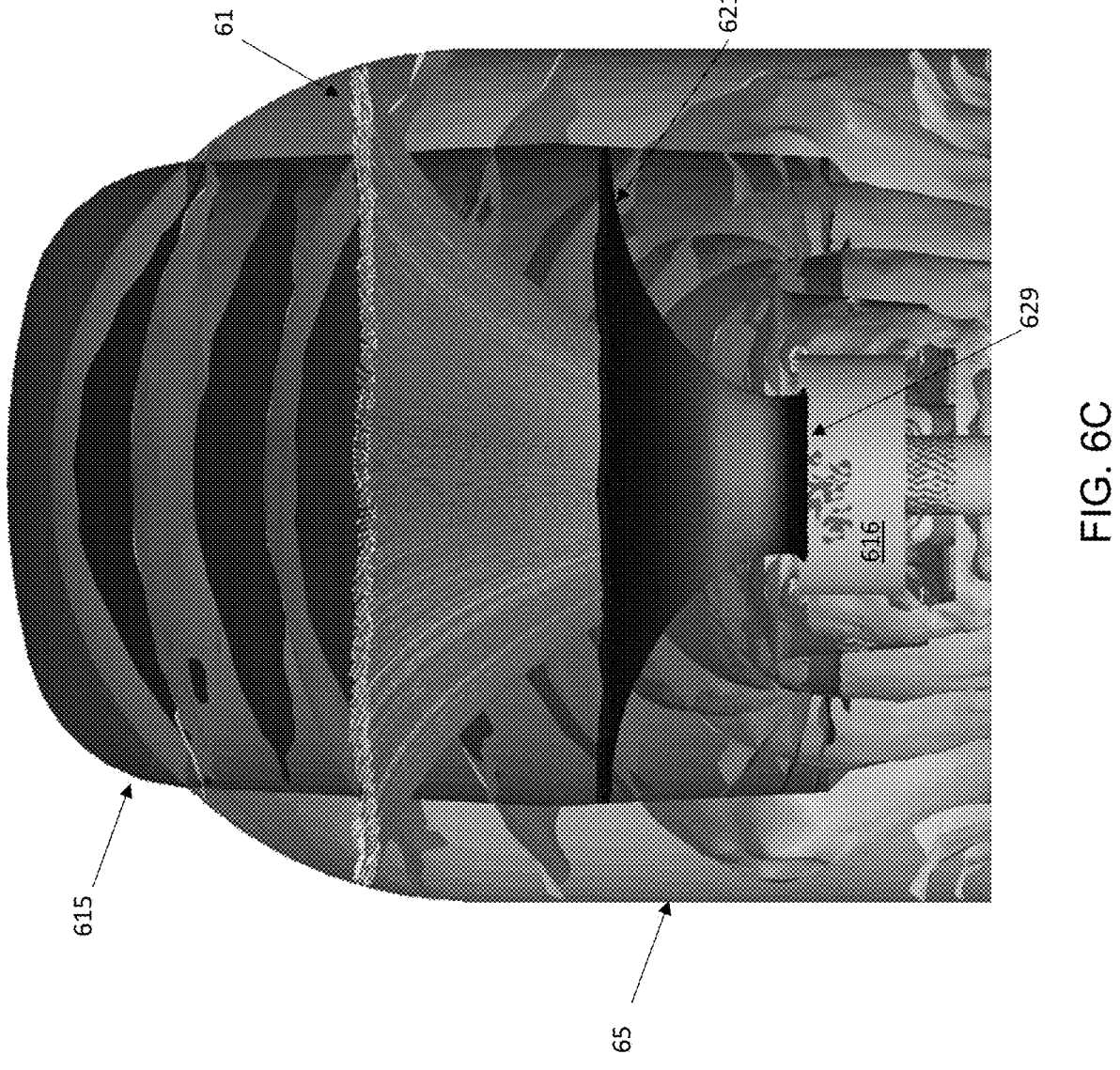
FIG. 6C is a simulation of charged particle trajectories for the detector systems of FIGS. 6A and 6B.

FIG. 6C demonstrates a comparison of two chambers, a prior art chamber 65, and an example smaller diameter and smaller volume chamber 615. The collection extent field lines for each system were computed, and overlaid so that the same detector and detector holder geometer 616 is common to both simulations. For the prior art chamber 65, the collection extent field lines are rendered with thickness to visually illustrate the division between the capture volumes above/bounded by the cone/trumpet of the collection extent field lines. Despite the much larger total volume of the prior chamber 65, the example chamber 615 with the collection extent field lines 621 is able to provide a larger capture volume.

Figure 7:
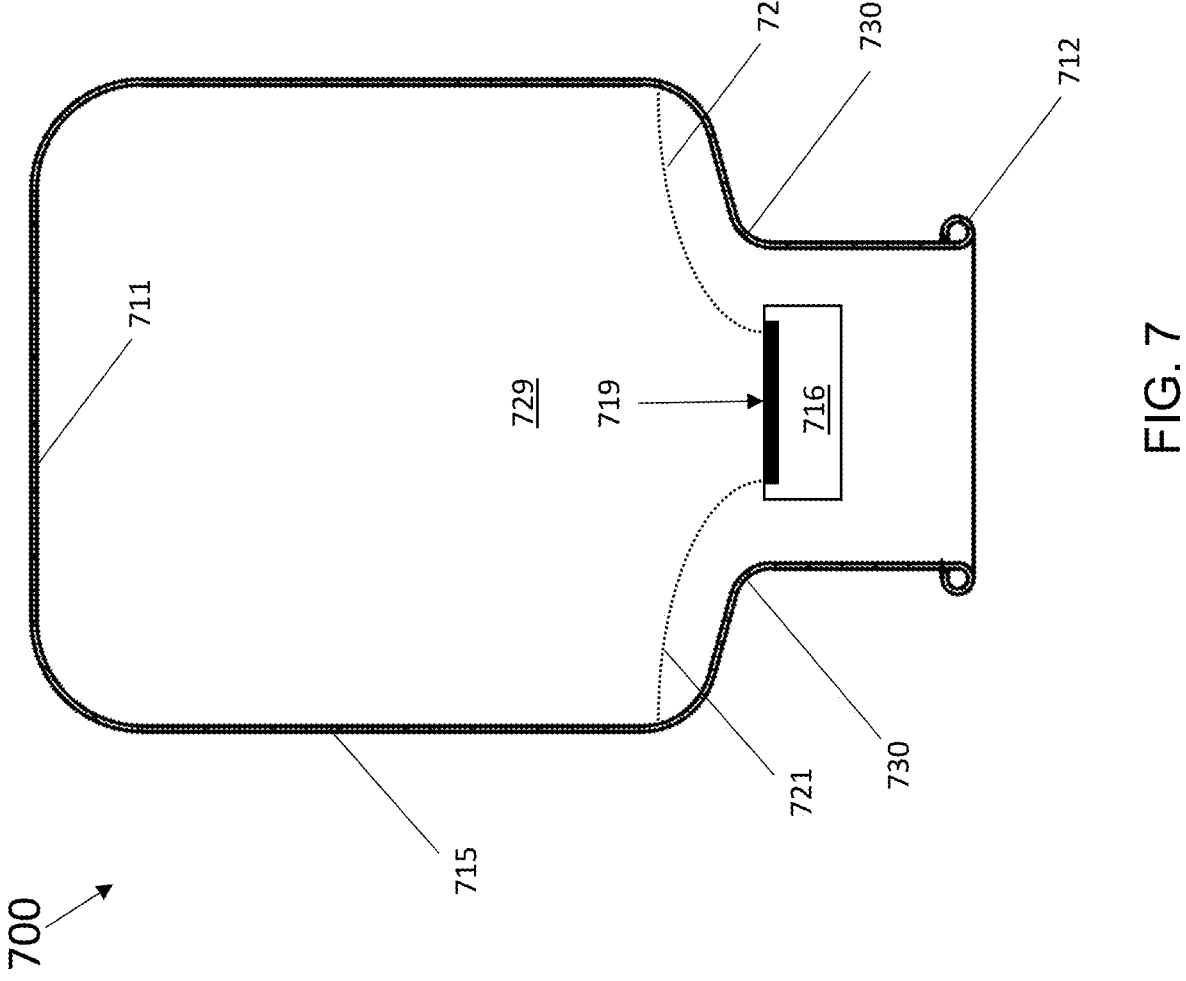
FIG. 7 is a cross-sectional schematic of yet another electrostatic precipitation detector example of the present disclosure.

FIG. 7 shows a detector chamber system 700 that includes a chamber 715 with a closed end 711 and an open end 712 and a target surface 719 held by a detector structure 716 in the open end 712 of the chamber 715. The chamber 715 is effectively the shape of an upside down bottle with the details shown being axisymmetric about a central longitudinal axis of the chamber 715. The open end 712 of the chamber 715 is formed as a constriction in the chamber wall and the bends in the chamber form convex surfaces 730 that encircle the target surface 719. When a voltage difference is stablished between the target surface 719 and the chamber 715, collection extent field lines 721 extend from the target surface 719 to the chamber 715 and are influence by the encircling convex surface 730 to bend laterally outward significantly and generate a capture volume 729 within the chamber 715 that contains almost all of the volume of the chamber 715 above the target surface 719.

While the examples shown herein illustrate a single convex surface that encircles the target surface, multiple convex structures can be used. In addition, while the convex surfaces shown herein are integrated with or at least coupled directed to a chamber, other implementations are convinced of, such as integrated with the detector structure or otherwise located about the target surface to bend the collection extent field lines impinging on the periphery of the target surface laterally away from the target surface.

Radon Gas Detector Systems and Methods

Examples of the present disclosure including using detection chambers with electrostatic lens features surrounding detectors, such as silicon detectors, to detect the presence and concentration of radon gas in the detection chamber using alpha spectrometry. The detection of radon gas using alpha spectrometry is a technique that relies on the distinctive characteristics of alpha particles emitted during the radioactive decay of radon and its decay products. Radon is a radioactive gas that releases alpha particles during its decay process. These alpha particles are relatively heavy, positively charged, and have limited penetrating power, making them ideal candidates for precise detection using electrostatic precipitation.

Alpha spectrometry involves several steps. First, air containing radon is collected within a detection chambers wherein decay products are formed, such as positively charged polonium 218, which quickly decays via alpha emission and, further in the chain, forms polonium 214, which also quickly decays via alpha emission. Using electrostatic precipitation, the charged the alpha-emitting radon progeny settle onto a collection surface within the detection chamber. The collection surface surface can include a thin film or a solid-state detector with the ability to capture and retain the alpha-emitting particles.

Once the radon progeny are collected, the solid-state detector is carefully analyzed. This involves measuring the energy and intensity of the alpha particles emitted during the decay process. Each alpha-emitting radon progeny has a characteristic energy spectrum, which serves as a fingerprint for identification. By analyzing these spectra in view of a known airflow rate and chamber volume, the concentration of radon and its progeny can be measure as well as their specific isotopic composition. Alpha spectrometry can be exceptionally sensitive. Even trace amounts of radon and its progeny can be detected due to the highly focused ionization and short range of alpha particles.

In operation, gas that contains radon is present in an electrostatic precipitation detector chamber and the short-lived decay products of radon are directed along field lines to settle onto a collection surface. The collection surface can be a solid material or a special detector designed to capture alpha particles. The collection surface is carefully analyzed using an alpha spectrometer. The alpha spectrometer can be formed as silicon detector at or adjacent to the surface that measures the energies and intensities of the alpha particles emitted by the deposited radon decay products. Silicon detectors offer high sensitivity, precise energy measurement capabilities, and the ability to discriminate between different types of captured particles. The energy spectrum obtained from the alpha spectrometer is unique to the specific isotopes present in the decay chain of radon. Each alpha-emitting decay product produces characteristic peaks in the energy spectrum, allowing for identification and quantification. By analyzing the energy peaks and their intensities, the types and concentrations of radon decay products present on the surface can be determined. From this information, aspects of the present disclosure implementing alpha spectrometric detection can infer the level of radon gas in the environment of interest.

Alpha spectrometry's sensitivity enables detection of extremely low levels of radon gas due to the ionizing power of alpha particles and their short range. Alpha spectrometry using silicon detectors can use a high-purity crystalline silicon material as a sensor. When an alpha particle interacts with the silicon, it loses energy and generates electron-hole pairs within the silicon lattice. This process produces a small electrical signal proportional to the energy of the incident alpha particle. The silicon detector is connected with sensitive electronics that measure the small electrical signals produced by the interaction of alpha particles with the silicon. These signals are converted into energy spectra, which represent the distribution of alpha particle energies. The energy spectrum obtained from the silicon detector is characterized by distinctive energy peaks corresponding to the different alpha-emitting radon decay products present in the sample. Each peak corresponds to a specific alpha particle energy, providing a unique signature for identification. By analyzing the positions and intensities of these energy peaks, the concentrations of various radon decay products present on the detector surface ben be quantified and from these concentrations, the level of radon gas in the detection chamber can be precisely estimated.

Figure 8:
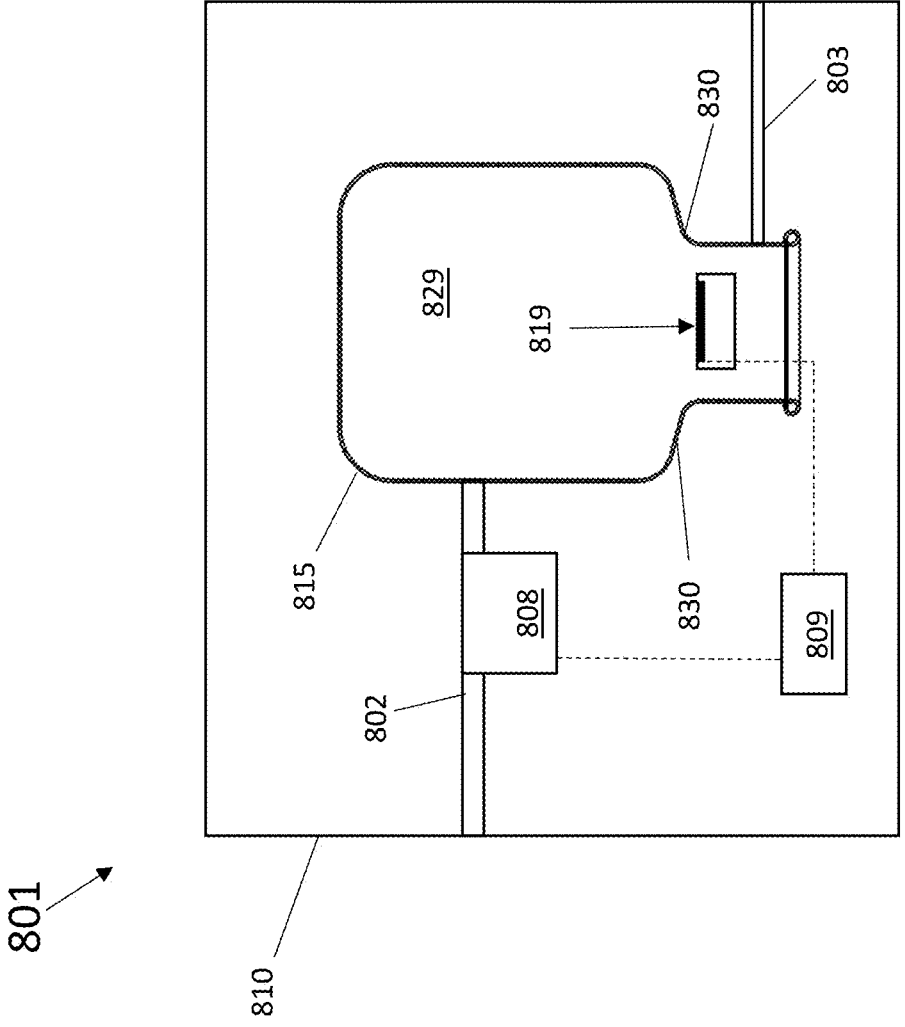
FIG. 8 is a schematic of a radon gas detector system including the electrostatic precipitation detector system of FIG. 7.

FIG. 8 shows a radon detector system 801 that includes a housing 810 containing an air-sampling chamber 815 and target surface 819 in a similar arrangement as the system of FIG. 7. The system 801 includes an inlet 802 to the chamber 815 and an outlet 803. The chamber 815 is made from a conductive material, such as stainless steel and the target surface 819 is a silicon-wafer-based detector configured to sense the emission energies of alpha particles emitted from particles captured on the target surface. In operation, a voltage difference is established between the chamber 815 and the target surface 819 and charged particles within the resultant capture volume 829 above the target surface 819 are directed along field lines to the target surface. The chamber 815 includes a convex surface encircling the target surface 819 according to aspects of the present disclosure. The system 801 also includes a controller 809 in electrical communication with the target surface 819 to receive information regarding the detector alpha emissions and calculate a radon concentration of the air within the chamber 815. The system 801 can include a sampling system 808 that has a pump to facilitate precise movement of air into the chamber 815, and the system 801 can also include additional operational features, such as a touchscreen or other user interface as well as additional sensors in the sample air paths 802, 803 and chamber 815.

Methods for Designing Electrostatic Precipitation System

Examples of the present disclosure include methods for designing measurement chambers, including measurement chamber shape and the arrangement of conductive surfaces around a target surface that improve the collection of charged particles on the target surface from within the chamber. Examples of the method include tracing electric field lines beginning from the target surface backwards (e.g., with respect to particle motion) through a solved three-dimensional electric field within an air-sampling chamber. Examples design methods include dividing, using computer-assisted design software and/or physical simulation software, an entire volume of an air-sampling chamber into cells or volume elements (e.g., voxels), each of which can be determined as being on a field line traced or not contributing to particles landing on a detector surface within the air-sampling chamber. Further, example methods also include optimizing the transit time of charged particles within the chamber arriving at the detector surface, by evaluating the travel distance along field lines and assigning a distance weighting function to the 3D volume elements. Examples of the present disclosure also include further measurement chambers having improved metrics when measured by the distance weighting function.

One skilled in the art will appreciate further features and advantages of the disclosures based on the provided for descriptions and embodiments. Accordingly, the inventions are not to be limited by what has been particularly shown and described. All publications and references cited herein are expressly incorporated herein by reference in their entirety.

Examples of the above-described embodiments can include the following:

1. An electrostatic precipitation instrument comprising:
    a conductive vessel defining a volume configured to receive a gaseous fluid sample, the conductive vessel defining an interior region of the volume configured to have a particle detector disposed therein;
    a detector surface disposed within the interior region and configured to detect particles thereon, wherein the conductive vessel and the detector surface are configured to maintain a voltage difference therebetween, the voltage difference generating electric field lines along which charged particles within the volume will be directed towards the detector surface, a portion of the field lines extending from an interior surface of the conductive vessel to the detector surface;
    a conductive convex surface of an inner wall of the conductive vessel configured to increase the curvature of field lines above the detector surface and thereby define a portion of the volume of the conductive vessel from which charged particles within a gaseous fluid sample can be captured by the detector surface.

2. The instrument of example 1, wherein the conductive convex surface is configured to increase the curvature of the field lines above the detector surface with respect to the influence of adjacent inner surface regions of the conductive vessel.

3. The instrument of examples 1 or 2, wherein the detector surface is configured to detect particles using alpha spectrometry.

4. The instrument of any of examples 1 to 3, wherein the conductive surface forms a portion of an interior surface of the conductive vessel.

5. The instrument of any of examples 1 to 4, wherein the conductive convex surface is integrally formed with adjacent inner surface portions of the conductive vessel.

6. The instrument of any of examples 1 to 5, wherein the conductive convex surface encircles the detector surface such that the conductive convex surface is configured increase the curvature of the field lines away from an axis normal to the detector surface.

7. The instrument of any of examples 1 to 6, wherein the conductive vessel defines a nominal width above the detector surface, and wherein the conductive convex surface defines a width less than the nominal width.

8. The instrument of any of examples 1 to 7, wherein the convex surface extends above a height of the detector surface.

9. The instrument of any of examples 1 to 8, wherein the conductive vessel has a circular cross-section and wherein the conductive surface defines a circular ring about the detector surface.

10. An electrostatic precipitation instrument for detecting radon gas, the instrument comprising:
    a conductive vessel defining a volume configured to receive a gaseous fluid sample, the conductive vessel defining a convex surface encircling an interior region of the volume configured to have a particle detector disposed therein;
    a detector surface disposed within the interior region and configured to detect polonium particles thereon using alpha spectrometry,
    wherein the conductive vessel and the detector surface are configured to maintain a voltage difference therebetween, the voltage difference generating electric field lines along which charged particles within the volume will be directed towards the detector surface, a portion of the field lines extending from an interior surface of the conductive vessel to the detector surface;
    wherein, when the voltage difference between the conductive vessel and the detector surface is established, the convex surface forms an electrostatic lens above the detector surface, the electrostatic lens being configured to influence the curvature of field lines above the detector surface and thereby define a portion of the volume of the conductive vessel from which charged particles from a gaseous fluid sample within conductive vessel can be captured by the detector surface.

11. The instrument of example 10, wherein the conductive convex surface is configured to increase the curvature of the field lines above the detector surface with respect to the influence of adjacent inner surface regions of the conductive vessel.

12. The instrument of examples 10 or 11, wherein the conductive vessel defines a nominal width above the detector surface, and wherein the conductive convex surface defines a width less than the nominal width.

13. The instrument of any of examples 10 to 12, wherein the convex surface extends equal to or above a height of the detector surface.

14. The instrument of any of examples 10 to 13, wherein the conductive vessel has a circular cross-section and wherein the conductive surface defines a ring about the detector surface.

15. The instrument of any of examples 10 to 14, wherein convex surface defines a transition between a nominal width region of the conductive vessel and a reduced width region, and wherein the detector surface is disposed within the reduced width region.

16. The instrument of any of examples 1 to 15, wherein the conductive vessel defines a closed end having a hemispherical shape.

17. The instrument of claim 16, wherein the detector surface is disposed opposite to the closed and with the surface facing the close end.

18. The instrument of any of examples 1 to 17, further comprising an air handling system coupled with the chamber and configured to control delivery of gas into and out of the conductive vessel.

19. The instrument of any of examples 1 to 18, wherein the detector surface is configured for real-time detection of radon gas in the volume of the conductive vessel.

20. The instrument of any of examples 1 to 19, wherein the detector surface comprises a silicon-wafer-based detector configured to sense the emission energies of alpha particles emitted from particles captured on the target surface.

What is claimed is:

1. An electrostatic precipitation instrument comprising:
   a conductive vessel defining a volume configured to receive a gaseous fluid sample, the conductive vessel defining an interior region of the volume configured to have a particle detector disposed therein;
   a detector surface disposed within the interior region and configured to detect particles thereon, wherein the conductive vessel and the detector surface are configured to maintain a voltage difference therebetween, the voltage difference generating electric field lines along which charged particles within the volume will be directed towards the detector surface, a portion of the field lines extending from an interior surface of the conductive vessel to the detector surface; and
   a conductive convex surface of an inner wall of the conductive vessel configured to increase the curvature of field lines above the detector surface and thereby define a portion of the volume of the conductive vessel from which charged particles within a gaseous fluid sample can be captured by the detector surface.

2. The instrument of claim 1, wherein the conductive convex surface is configured to increase the curvature of the field lines above the detector surface with respect to the influence of adjacent inner surface regions of the conductive vessel.

3. The instrument of claim 1, wherein the detector surface is configured to detect particles using alpha spectrometry.

4. The instrument of claim 1, wherein the conductive surface forms a portion of an interior surface of the conductive vessel.

5. The instrument of claim 4, wherein the conductive convex surface is integrally formed with adjacent inner surface portions of the conductive vessel.

6. The instrument of claim 1, wherein the conductive convex surface encircles the detector surface such that the conductive convex surface is configured increase the curvature of the field lines away from an axis normal to the detector surface.

7. The instrument of claim 1, wherein the conductive vessel defines a nominal width above the detector surface, and wherein the conductive convex surface defines a width less than the nominal width.

8. The instrument of claim 1, wherein the convex surface extends above a height of the detector surface.

9. The instrument of claim 1, wherein the conductive vessel has a circular cross-section and wherein the conductive surface defines a circular ring about the detector surface.

10. An electrostatic precipitation instrument for detecting radon gas, the instrument comprising:
    a conductive vessel defining a volume configured to receive a gaseous fluid sample, the conductive vessel defining a convex surface encircling an interior region of the volume configured to have a particle detector disposed therein; and
    a detector surface disposed within the interior region and configured to detect polonium particles thereon using alpha spectrometry,
    wherein the conductive vessel and the detector surface are configured to maintain a voltage difference therebetween, the voltage difference generating electric field lines along which charged particles within the volume will be directed towards the detector surface, a portion of the field lines extending from an interior surface of the conductive vessel to the detector surface;
    wherein, when the voltage difference between the conductive vessel and the detector surface is established, the convex surface forms an electrostatic lens above the detector surface, the electrostatic lens being configured to influence the curvature of field lines above the detector surface and thereby define a portion of the volume of the conductive vessel from which charged particles from a gaseous fluid sample within conductive vessel can be captured by the detector surface.

11. The instrument of claim 10, wherein the conductive convex surface is configured to increase the curvature of the field lines above the detector surface with respect to the influence of adjacent inner surface regions of the conductive vessel.

12. The instrument of claim 10, wherein the conductive vessel defines a nominal width above the detector surface, and wherein the conductive convex surface defines a width less than the nominal width.

13. The instrument of claim 10, wherein the convex surface extends equal to or above a height of the detector surface.

14. The instrument of claim 10, wherein the conductive vessel has a circular cross-section and wherein the conductive surface defines a ring about the detector surface.

15. The instrument of claim 10, wherein the convex surface defines a transition between a nominal width region of the conductive vessel and a reduced width region, and wherein the detector surface is disposed within the reduced width region.

16. The instrument of claim 10, wherein the conductive vessel defines a closed end having a hemispherical shape.

17. The instrument of claim 16, wherein the detector surface is disposed opposite to the closed and with the surface facing the close end.

18. The instrument of claim 10, further comprising an air handling system coupled with the chamber and configured to control delivery of gas into and out of the conductive vessel.

19. The instrument of claim 10, wherein the detector surface is configured for real-time detection of radon gas in the volume of the conductive vessel.

20. The instrument of claim 10, wherein the detector surface comprises a silicon-wafer-based detector configured to sense the emission energies of alpha particles emitted from particles captured on the target surface.

* * * * *